United States Patent [19]

Narayanan et al.

[11] 3,951,950

[45] Apr. 20, 1976

[54] 4-AZATRICYCLO[4.3.1.1$^{3,8}$]UNDECANE AND RELATED COMPOUNDS

[75] Inventors: Venkatachala Lakshmi Narayanan, Hightstown; Linda Louise Setescak, Cranbury, both of N.J.

[73] Assignee: E. R. Squibb & Sons, Inc., Princeton, N.J.

[22] Filed: Mar. 5, 1973

[21] Appl. No.: 337,963

Related U.S. Application Data

[62] Division of Ser. No. 754,460, Aug. 21, 1968, Pat. No. 3,763,165.

[52] U.S. Cl. ............... 260/239 B; 424/244; 424/246; 424/248; 424/250; 424/267; 424/274; 260/239 BF; 260/247.5 H; 260/243 B; 260/268 TR; 260/293.59; 260/326.81
[51] Int. Cl.$^2$ ............................ C07D 223/14
[58] Field of Search ........................... 260/239 B

[56] References Cited
UNITED STATES PATENTS
3,631,165  12/1971  Berezin ................ 260/239 B

*Primary Examiner*—Alton D. Rollins
*Assistant Examiner*—Mark L. Berch
*Attorney, Agent, or Firm*—Lawrence S. Levinson; Merle J. Smith

[57] ABSTRACT

This invention relates to a novel series of compounds characterized particularly by the azatricyclo[4.3.1.1$^{3,8}$]undecane ring. These include 4-azatricyclo[4.3.1.1$^{3,8}$]undecan-5-one, 4-azatricyclo[4.3.1.1$^{3,8}$]undecane and nitrogen substituted derivatives of each of these and their salts. The compounds are useful as antiviral, cardiovascular or antiinflammatory agents, or as intermediates for such substances.

7 Claims, No Drawings

4-AZATRICYCLO[4.3.1.1³,⁸]UNDECANE AND RELATED COMPOUNDS

RELATED APPLICATION

This application is a division of copending application Ser. No. 754,460, filed Aug. 21, 1968, U.S. Pat. No. 3,765,165, Oct. 2, 1973.

SUMMARY OF THE INVENTION

This invention relates to the novel intermediate 4-azatricyclo [4.3.1.1³,⁸]undecan-5-one (derived by rearrangement of 2-adamantane oxime) which may be depicted as follows:

(I) 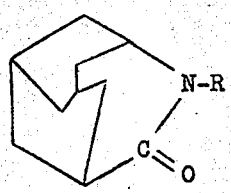

R is hydrogen. The intermediate of formula I may then either be reduced to 4-azatricyclo[4.3.1.1³,⁸]undecane of the formula (II) 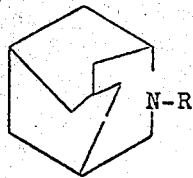

R being hydrogen, or reacted with a compound R-hal, in which R has the meaning defined below other than hydrogen, to obtain a 4-azatricyclo[4.3.1.1³,⁸]undecan-5-one derivative of the formula (III) 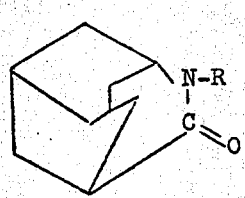

R being other than hydrogen. The compound of formula II may be reacted with a compound R-hal, in which R is other than hydrogen, or the compound of formula III may be reduced, both reactions giving 4-azatricyclo[4.3.1.1³,⁸]undecane derivatives of the formula (IV) 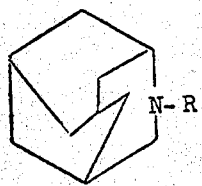

The symbol R used above represents hydrogen, lower alkyl, lower alkenyl, cycloalkyl-lower alkyl, the cycloalkyl group having 3 to 7 carbon atoms, aralkyl, $(CH_2)_m$-COOH or $(CH_2)_n$-B. $m$ is an integer from 1 to 10 and $n$ is an integer from 2 to 10. The term "hal" refers to any of the halogens, preferably chlorine or bromine.

B represents a basic, nitrogen-containing radical containing 15 or less atoms in the radical. B may represent the

group in which the latter group represent a 5- to 7-membered saturated nitrogen heterocyclic, the $R_1$ and $R_2$ joining with the nitrogen to form the heterocyclic, for example, pyrrolidino, piperidino, homopiperidino, piperazino, morpholino or thiamorpholino. In addition, the heterocyclic may bear one or two groups such as lower alkyl, lower alkoxy, halo, trihalomethyl, lower alkanoyloxy-lower alkyl or hydroxy-lower alkyl.

The lower alkyl groups represented by the symbols include straight and branched chain saturated hydrocarbon radicals of less than 8 carbon atoms, such as methyl, ethyl, propyl, isopropyl, butyl, isobutyl, t-butyl or the like and the lower alkenyl groups include similar monounsaturated groups such as vinyl, allyl, isopropenyl, butenyl, isobutenyl, etc. The cycloalkyl groups include cyclopropyl, cyclobutyl, cyclopentyl, cyclohexyl and cycloheptyl. These are attached to lower alkyl groups of the type described. The aralkyl groups are primarily phenyl-lower alkyl groups in which the phenyl may be substituted by one or two halogen atoms, which may be any of the four halogens but especially chlorine or bromine, lower alkyl groups such as those enumerated above or lower alkoxy groups such as methoxy, ethoxy, propoxy or the like.

The symbols $R_1$ and $R_2$ in the group

may be the same or different representing hydrogen, lower alkyl or hydroxy-lower alkyl groups such as those referred to above. Illustrative of the group

are amino, methylamino, ethylamino, dimethylamino, diethylamino, dipropylamino, methyl(ethyl)amino, di(hydroxyethyl)amino and the like.

The

group may also form a heterocyclic radical. The symbols $R_1$ and $R_2$ may together represent the carbon (and hydrogen) and the oxygen, sulfur or nitrogen atoms which, with the nitrogen atom in the above group, form a 5-, 6- or 7-membered nitrogen heterocyclic containing not more than one hetero atom in addition to the nitrogen already shown in the group. These heterocyclic radicals may also bear one to three of the following substituents: halogen, trifluoromethyl, lower alkoxy, lower alkyl, hydroxy-lower alkyl such as hydroxymethyl, 2-hydroxyethyl or the like, hydroxylower alkoxy-lower alkyl such as 2-(2-hydroxyethoxy)ethyl or the like, alkanoyloxy-lower alkyl (up to about 14 carbons in the alkanoyl group) such as 2-heptanoyloxyethyl, carbo-lower alkoxy such as carbomethoxy, carboethoxy, carbopropoxy or the like, or 2-(alkanoyloxy-lower alkoxy)lower alkyl (with up to about 14 carbons in the alkanoyl group) such as 2-(decanoyloxyethoxy)ethyl or the like.

Illustrative of the heterocyclic radicals represented by

are the following: piperidino; (lower alkyl)piperidino [e.g., 2-, 3-, or 4-(lower alkyl)piperidino]; di(lower alkyl)piperidino [e.g., 2,4-, 2,5- 3,5-di(lower alkyl)piperidino]; (lower alkoxy)piperidino; [e.g., 2-methoxypiperidino or 3-methoxypiperidino]; hydroxypiperidino [e.g., 3-hydroxy- or 4-hydroxypiperidino]; pyrrolidino (lower alkyl)pyrrolidino [e.g., 3-methylpyrrolidino]; di(lower alkyl)pyrrolidino [e.g., 3,4-dimethylpyrrolidino]; (lower alkoxy)pyrrolidino [e.g., 2-methoxypyrrolidino]; morpholino; (lower alkyl)morpholino [e.g., 3-methylmorpholino]; di(lower alkyl)morpholino [e.g., 3,5- dimethylmorpholino]; (lower alkoxy)morpholino [e.g., 2-methoxymorpholino]; thiamorpholino; (lower alkyl)thiamorpholino [e.g., 3-methylthiamorpholino]; di(lower alkyl)thiamorpholino [e.g., 3,5-dimethylthiamorpholino]; (lower alkoxy)thiamorpholino [e.g., 3-methoxythiamorpholino]; piperazino; (lower alkyl)piperazino [e.g., $N^4$-methylpiperazino]; di(lower alkyl)piperazino [e.g., 2,5-dimethylpiperazino or 2,6-dimethylpiperazino]; (lower alkoxy)piperazino alkyl)piperazino e.g., 2-methoxypiperazino]; (hydroxy-lower alkyl)piperazino [e.g., $N^4$-(2-hydroxyethyl)piperazino]; (alkanoyloxylower alkyl)piperazino wherein the alkanoyloxy group has up to .14 carbons; [e.g., $N^4$-(2-heptanoyloxyethyl)piperazino or $N^4$- (2-dodecanoyloxyethyl)piperazino]; (hydroxy-lower alkoxy-lower alkyl)piperazino [e.g., $N^4$-(2-hydroxyethoxyethyl)piperazino]; and (carbo-lower alkoxy)piperazino. [e.g., $N^4$-(carbomethoxy-, carboethoxy-, or carbopropoxy)piperazino; homopiperazino; or $N^4$-(2-hydroxyethyl)-homopiperazino].

The particularly preferred compounds are those wherein R is hydrogen, 3-(4-methyl-1-piperazinyl)propyl, allyl or phenethyl.

The compounds of formula IV form acid addition salts with various inorganic and organic acids. These salts frequently provide convenient means for separating the product from the reaction mixture in which it is produced or from the solvent in which it is produced or from the solvent in which it is extracted in view of their insolubility in various media. Thus the product may be precipitated in the form of an insoluble salt and converted, by conventional techniques, to the free base or to another salt if desired.

Illustrative salts include the hydrohalides, such as hydrochloride, hydrobromide and hydroiodide, especially the first two, other mineral acid salts such as phosphate, sulfate, nitrate, etc., organic acid salts such as oxalate, tartrate, malate, maleate, citrate, camphorsulfonate, methanesulfonate, benzenesulfonate, toluenesulfonate, salicylate, benzoate, ascorbate, mandelate, pamoate or the like.

The compounds of formula IV and their physiologically acceptable salts are useful as antiviral, cardiovascular or antiinflammatory agents to treat or alleviate the symptoms in various warm blood animals. While all of the class in general exhibits these properties, those compounds wherein R is a lower alkenyl, cycloalkyl-lower alkyl or aralkyl group have antiviral activity as the predominant property; those compounds wherein R is

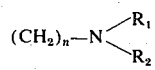

have cardiovascular activity as the predominant property and those compounds wherein R is $(CH_2)_m$-COOH have antiinflammatory activity as the predominant property.

As anti-inflammatory agents, the compounds of this invention may be used topically in lieu of and in the same manner as cortisone in the treatment of acute inflammatory and allergic conditions of the eye, skin or mucosa, e.g., as suspension, ointment or cream containing about 0.1 to about 2.5%, by weight, of a compound of formula IV or salt thereof. In the rabbit, for example, a 1% ointment is applied to the skin area 3 to 4 times daily.

To arrest cardiac arrhythmias, the compounds of this invention are incorporated in conventional oral or parenteral dosage forms for administration in single or divided doses of about 4 to 50 mg/kg/day, preferably about 5 to 20 mg/kg/day 2 to 4 times daily. For example, in mice about 10mg/kg/orally are used.

About 4 to 50 mg/kg/day, preferably about 5 to 25 mg/kg/day, used orally or parenterally in two to six divided doses, may be used to combat influenza virus such as A-FR8 or hepatic virus such as $MHV_3$. For example, about 5 to 15 mg/kg, in an injectable vehicle, may be used two to four times daily against influenza virus in mice.

The compounds of formula IV or their physiologically acceptable acid addition salts may be administered by incorporation in conventional forms such as tablets, capsules, elixirs or suspensions for oral administration, in sterile solution or suspension for parenteral administration, or in ointment, cream or lotion for topical use. The dosage form is formulated according to conventional practice including carriers, adjuvants, excipients, lubricants, stabilizers, etc. as required. About 0.1 to about 90% by weight of the active substance may be included. For oral administration a tablet or gelatin capsule containing about 5 to about 95 per cent by weight of active material, e.g., about 5 to 500 mg., and the remainder conventional adjuvants may be made up. An aqueous suspension or syrup containing about 0.5 to 10 per cent of active material may also be used. Sterile injectable solutions or suspensions may be made up containing about 0.5 to 25%, preferably about 5 to 10 percent, by weight of active substance in an aqueous vehicle such as sterile water for injection, saline or the like, or in an oil such as a vegetable oil like peanut oil, sesame oil or the like. For topical use, an ointment or cream containing about 0.1 to 2.5%, by weight of active substance in cream or ointment base as found in a standard pharmacy text such as Remington's Practice of Pharmacy may be used.

To produce the new compounds of this invention 1-hydroxyadamantane is treated with concentrated sulfuric acid to obtain 2-adamantanone. The latter is reacted with hydroxylamine hydrochloride or sulfate to give 2-adamantanone oxime. The oxime of 2-adamantanone, by Beckmann rearrangement with excess polyphosphoric acid, phosphorous pentachloride or the like, at 120°–130°C, yields 4-azatricyclo[4.3.1.1$^{3,8}$]undecan-5-one of formula I.

Reduction of the lactam of formula I, e.g., by refluxing with lithium aluminum hydride in an inert solvent like ether, tetrahydrofuran, dimethoxyethane or the like, gives 4-azatricyclo[4.3.1.1$^{3,8}$]undecane of formula II. The latter, when alkylated with a compound R-hal yields the 4-azatricyclo[4.3.1.1$^{3,8}$]undecane derivatives of formula IV.

If, however, the lactam of formula I is first alkylated with a compound R-hal, the 4-azatricyclo[4.3.1.1$^{3,8}$]undecan-5-one derivatives of formula III are obtained and these in turn may be reduced with lithium aluminum hydride as described above to obtain by this alternative route the same compounds of formula IV.

The following examples are illustrative of the invention. All temperatures are on the centigrade scale.

EXAMPLE 1

Oxime of 2-adamantanone

To a cooled solution of 8.5 gm. (0.05 mole) of 2adamantanone, 6.2 gm. (0.09 mole) of hydroxylamine-hydrochloride and 16 ml. of water, 11.2 gm. (0.28 mole) of sodium hydroxide are added with stirring. The mixture is refluxed for 10 minutes. After cooling the contents are poured onto 300 ml. of 1 N HCl. The precipitate which forms is filtered, giving 5.3 gm. (57%) of the oxime of 2-adamantanone as white crystals; m.p.160°–164°C., λ Nujol$^{max}$ 1672 cm$^{-1}$ (C=N).

EXAMPLE 2

4-Azatricyclo[4.3.1.1$^{3,8}$]undecan-5-one

A manually stirred mixture of 3 gm. (0.018 mole) of the oxime of 2-adamantanone and 90 gm. of polyphosphoric acid is placed in an oil bath preheated to 140°C. The temperature of the mixture is held between 120°–130°C. for 10 minutes. At the end of the period, the dark brown solution is cooled and treated with 500 ml. of water. The mixture is extracted with 500 ml. of chloroform, dried (MgSO$_4$) and evaporated, giving 1.4 gm. of crude white solid. Sublimation of the product gives 1.17 gm. (39%) of white crystals of 4-azatricyclo[4.3.1.1$^{3,8}$]undecan-5-one, melting at >270°C., λ Nujol$^{max}$ 1650 cm$^{-1}$ (C=O), $\tau$CDCL$_3$ 7.5 – 8.4 (adamantyl protons), 6.4 – 7.5 (N-H and methine hydrogen adjacent to carbonyl).

Anal. Calcd. for C$_{10}$H$_{15}$NO: C, 72.69; H, 9.15; N, 8.48. Found: C, 72.98; H, 9.00; N, 8.43.

EXAMPLE 3

4-[3-(4-methyl-1-piperazinyl)propyl]-4-azatricyclo[4.3.1.1$^{3,8}$]-undecan-5-one To a well stirred solution of 2.4 gm. (0.02 mole) of 4-azatricyclo[4.3.1.1$^{3,8}$]undecan-5-one in 300 ml. of toluene, 3.2 gm. of powdered sodium hydroxide are added. After 5 minutes of vigorous stirring, 12 gm. of 1-(3-bromopropyl)-4-methylpiperazine dihydrobromide are added and the mixture heated for 20 minutes on a steam bath. The reaction mixture is cooled and stirred with 50 ml. of cold water. The toluene layer is separated, washed with 2 × 50 ml. of water and extracted with 3 × 100 ml. of 5 N HCl. The acid extracts are combined, washed with 100 ml. of ether, cooled and made basic with 2 N NaOH. The free base is extracted with 3 × 250 ml. of chloroform, dried (MgSO$_4$) and evaporated in vacuo to give 4-[3-(4-methyl-1-piperazinyl)propyl]-4-azatricyclo[4.3.1.1$^{3,8}$]undecan-5-one.

EXAMPLE 4

4-[3-(4-methyl-1-piperazinyl)propyl]-4-azatricyclo[4.3.1.1$^{3,8}$]undecane

To a cooled suspension of 1.5 gm. of lithium aluminum hydride in 50 ml. of tetrahydrofuran, 1.5 gm. (0.01 mole) of 4-[3-(4-methyl-1-piperazinyl)propyl]-5-azatricyclo[4.3.1.1$^{3,8}$]undecan-5-one in 50 ml. of tetrahydrofuran are added dropwise with stirring. The mixture is refluxed overnight. Excess lithium aluminum hydride is decomposed by the cautious addition of water to the cooled mixture. The gelatinous precipitate becomes granular after the addition of 30 ml. of 10% sodium hydroxide. The precipitate is filtered off and tetrahydrofuran is removed in vacuo from the filtrate. The residual material is extracted with 3 × 50 ml. of ether. The ether extract is dried over magnesium sulfate and the product, 4-[3-(4-methyl-1-piperazinyl)-propyl]-4-azatricyclo[4.3.1.1$^{3,8}$]undecane, is isolated by evaporation of the ether solution in vacuo.

EXAMPLE 5

4-Azatricyclo[4.3.1.1$^{3,8}$]undecane hydrochloride

To a cooled suspension of 0.37 gm. (0.01 mole) of lithium aluminum hydride in 10 ml. of dry tetrahydrofuran, 0.5 gm. (0.003 mole) of 4-azatricyclo[4.3.1.1$^{3,8}$]undecan--one in 10 ml. of dry tetrahydrofuran are added dropwise with stirring. The mixture is refluxed overnight. Excess lithium aluminum hydride is decomposed by the cautious addition of 10 ml. of water to the cooled mixture. The gelatinous precipitate becomes granular after the addition of 10 ml. of 10% NaOH. The precipitate is filtered and the tetrahydrofuran is removed from the filtrate. The residual material is extracted three times with 50 ml. of ether. The extract containing crude 4-azatricyclo[4.3.1.1$^{3,8}$]undecane is dried (MgSO$_4$) and a solution of HCl in ether is added until precipitation is complete. The crude salt, 0.300 gm. (53%) is crystallized from alcohol-ether to give 0.130 gm. (23%) of white crystalline 4-azatricyclo[4.3.1.1$^{3,8}$]-undecane hydrochloride, m.p. above 270°; λ Nujol$^{max}$ 2600 –2440$^{-1}$ (-NH$_2$) 1610 cm$^{-1}$ (m) (-NH$_2$+), $\tau$CDCl$_3$ 7.5 – 8.5 (adamantyl protons), 6.3 – 6.8 (CH$_2$ adjacent to NH$_2$+), 5.8 – 6.2 (CH adjacent to NH$_2$+), 8 – 9 (broad NH$_2$+).

Anal. Calcd. for $C_{10}H_{17}N\cdot HCl$: C, 63.99; H, 9.67; N, 7.47; Cl, 18.89 Found: C, 63.83; H, 10.00; N, 7.47; Cl. 18.85.

EXAMPLE 6
4-allyl-4-azatricyclo[4.3.1.1$^{3,8}$]undecane

To a well stirred solution of 1.2 gm. (0.01 mole) of allyl bromide in 50 ml. of benzene, a solution of 1.5 gm. (0.01 mole) of 4-azatricyclo[4.3.1.1$^{3,8}$]undecane in 50 ml. of benzene is added dropwise. The mixture is refluxed 1 hr., cooled, and 1 gm. of acetic anhydride is added. The mixture is refluxed an additional 2 hrs., cooled, poured into ice water and acidified with acetic acid. The layers are separated and the aqueous layer is extracted with ether. The acidic aqueous layer is made basic with NaOH, and extracted with chloroform. The chloroform extract is washed with water, dried over magnesium sulfate, filtered and the solvent evaporated to give 4-allyl-4-azatricyclo[4.3.1.1$^{3,8}$]undecane.

The following additional products of formulas III and IV may be obtained by substituting in the procedure of Example 3 for the 1-(3-bromopropyl)-4-methylpiperazine the compound listed in the middle column below. By otherwise following the procedure of that example, the product of formula III, wherein R is the group listed in the right hand column below, is obtained. Then by utilizing that product in the procedure of Example 4, the product of formula IV, wherein R is the same group listed in the right hand column, is obtained. Any acid addition salt may be obtained by the procedure of Example 5 utilizing hydrochloric acid or another inorganic or organic acid.

| Example | Reactant | R |
|---|---|---|
| 7 | $Cl-(CH_2)_2-N(CH_3)_2$ | $-(CH_2)_2-N(CH_3)_2$ |
| 8 | $Cl-(CH_2)_2-N(C_2H_5)_2$ | $-(CH_2)_2-N(C_2H_5)_2$ |
| 9 | $Br-(CH_2)_3-N(CH_3)_2$ | $-(CH_2)_3-N(CH_3)_2$ |
| 10 |  |  |
| 11 |  |  |
| 12 |  |  |
| 13 | $Cl-(CH_2)_2CH_3$ | $-(CH_2)_2CH_3$ |
| 14 | $Cl-(CH_2)_6CH_3$ | $-(CH_2)_6CH_3$ |
| 15 |  | 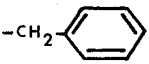 |
| 16 |  | 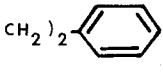 |
| 17 | 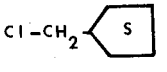 | 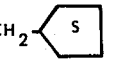 |
| 18 | 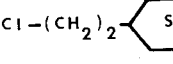 | 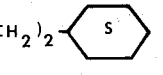 |
| 19 |  | 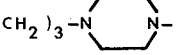 |
| 20 | 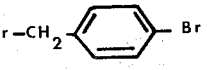 | 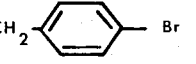 |
| 21 | 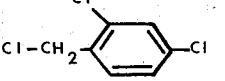 | 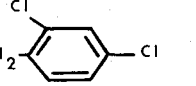 |

| Example | Reactant | R |
|---|---|---|
| 22 | Cl–CH$_2$–C$_6$H$_4$–CH$_3$ (m) | –CH$_2$–C$_6$H$_4$–CH$_3$ (m) |
| 23 | Cl–CH$_2$–C$_6$H$_4$–OCH$_3$ | –CH$_2$–C$_6$H$_4$–OCH$_3$ |
| 24 | Cl–(CH$_2$)$_4$–N(thiomorpholine) | –(CH$_2$)$_4$–N(thiomorpholine) |
| 25 | Cl–(CH$_2$)$_3$–N(morpholine) | –(CH$_2$)$_3$–N(morpholine) |

The following additional products of formula IV wherein R is the group in the right hand column below, may be obtained by the method of Example 6, substituting for the allyl bromide the reactant shown in the middle column below.

| Example | Reactant | R |
|---|---|---|
| 26 | Cl–(CH$_2$)$_{10}$–N(piperazine)NCH$_3$ | –(CH$_2$)$_{10}$–N(piperazine)NCH$_3$ |
| 27 | Cl—(CH$_2$)$_2$—COOH | —(CH$_2$)$_2$—COOH |
| 28 | Cl—(CH$_2$)$_9$—COOH | —(CH$_2$)$_9$—COOH |
| 29 | Cl–(CH$_2$)$_3$–N(morpholine) | –(CH$_2$)$_3$–N(morpholine) |
| 30 | Cl–(CH$_2$)$_2$–N(piperidine)–OCH$_3$ | –(CH$_2$)$_2$–N(piperidine)–OCH$_3$ |
| 31 | Cl–(CH$_2$)$_2$–N(piperazine)N–OC$_2$H$_5$ | –(CH$_2$)$_2$–N(piperazine)N–OC$_2$H$_5$ |
| 32 | Cl–(CH$_2$)$_2$–N(piperidine)–CF$_3$ | –(CH$_2$)$_2$–N(piperidine)–CF$_3$ |
| 33 | Cl–(CH$_2$)$_4$–N(thiomorpholine)–Cl | –(CH$_2$)$_4$–N(thiomorpholine)–Cl |
| 34 | Cl–(CH$_2$)$_2$–N(piperidine)–OCH$_3$ | –(CH$_2$)$_2$–N(piperidine)–OCH$_3$ |
| 35 | Cl—(CH$_2$)$_4$NHCH$_3$ | —(CH$_2$)$_4$NHCH$_3$ |
| 36 | Cl—CH(CH$_3$)CH$_2$N(CH$_3$)$_2$ | —CH(CH$_3$)CH$_2$N(CH$_3$)$_2$ |
| 37 | Cl—(CH$_2$)$_3$NH$_2$ | —(CH$_2$)$_3$NH$_2$ |
| 38 | Cl—CH(CH$_3$)—CH$_3$ | —CH(CH$_3$) |
| 39 | Cl—(CH$_2$)$_2$CH=CH$_2$ | —(CH$_2$)$_2$CH=CH$_2$ |
| 40 | Cl—CH$_3$ | —CH$_3$ |
| 41 | Cl—C$_2$H$_5$ | —C$_2$H$_5$ |
| 42 | Cl–(CH$_2$)$_2$NH–(adamantyl) | –(CH$_2$)$_2$NH–(adamantyl) |

What is claimed is:
1. A compound of the formula

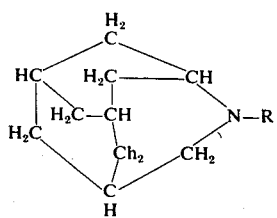

wherein R is $(CH_2)_m$-COOH and $m$ is an integer from 1 to 10.

2. A compound of the formula

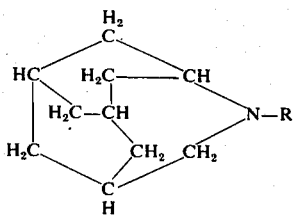

wherein R is phenyl-lower alkyl.

3. A compound as in claim 2 wherein the phenyl-lower alkyl group is phenethyl.

4. A compound of the formula

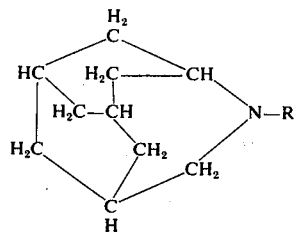

wherein R is cycloalkyl-lower alkyl; wherein the cycloalkyl group has from 3 to 7 carbon atoms.

5. A compound as in claim 4 wherein the cycloalkyl group is cyclohexyl.

6. A compound of the formula

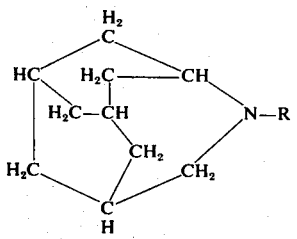

wherein R is lower alkenyl.

7. A compound as in claim 6 wherein the lower alkenyl group is allyl.

* * * * *